United States Patent [19]

Carbonnier

[11] Patent Number: 5,078,160
[45] Date of Patent: Jan. 7, 1992

[54] PROCESS AND DEVICES FOR TRANSFERRING COLORED PIGMENTS TO THE SKIN

[76] Inventor: Isabelle Carbonnier, 6, rue Arthur Honegger, 51100 Reims, France

[21] Appl. No.: 434,691
[22] PCT Filed: Feb. 9, 1989
[86] PCT No.: PCT/FR89/00051
§ 371 Date: Oct. 10, 1989
§ 102(e) Date: Oct. 10, 1989
[87] PCT Pub. No.: WO89/07407
PCT Pub. Date: Aug. 24, 1989

[30] Foreign Application Priority Data

Feb. 10, 1988 [FR] France ............................. 88 01666

[51] Int. Cl.⁵ ............................................. A45D 40/26
[52] U.S. Cl. ................................. 132/320; 132/333
[58] Field of Search ............... 132/319, 320, 333, 200

[56] References Cited

U.S. PATENT DOCUMENTS

| | | | |
|---|---|---|---|
| 2,735,435 | 2/1956 | Feinstein | 132/320 |
| 3,568,684 | 3/1971 | Reece | 132/333 |
| 4,383,539 | 5/1983 | Collins et al. | 132/320 |
| 4,611,611 | 9/1986 | Beal, Jr. | 132/320 |
| 4,751,934 | 6/1988 | Moir et al. | 132/319 |

FOREIGN PATENT DOCUMENTS 2152368  8/1985  United Kingdom ............... 132/320

Primary Examiner—Gene Mancene
Assistant Examiner—Michael Lynch
Attorney, Agent, or Firm—William A. Drucker

[57] ABSTRACT

Device for make-up by transfer of colored substances to the skin from a relatively soft support applied to the skin and removed after transfer, characterized in that said support (1) is in cut-out form, that the pigments or colored powder type lacquers of the cosmetic type are deposited thereon in order to form a pigmented area (regions 2 to 7) having the contour of a predetermined region of the skin, with a distribution of the various colored substances and of their density in said zone which are such as to produce the effect of the final make-up, the adherence of the pigments to one another and to the support being, in the surface layer, weaker than their adherence to the skin so that their transfer to the skin is effected by simple application of the support to the section of skin to be made up.

13 Claims, 4 Drawing Sheets

PROCESS AND DEVICES FOR TRANSFERRING COLORED PIGMENTS TO THE SKIN

Traditional methods for applying make-up to the skin are limited to brushes and pads combined with the stoppers of the make-up containers.

To facilitate the application thereof by clumsy persons or persons not endowed with an aesthetic sense, the patents FR A 941 489 and FR A 1 577 258 propose guiding the pencil or other make-up application means by means of a mask suitably cut out serving as stencil. Methods using a stencil correctly define the surface of the skin to be covered but compel the user to have recourse to traditional application means, leaving to the user the choice of colours and the arrangement thereof.

A transfer method is further described, in its application to the eyelids, in the U.S. Pat. No. 3,568,684: a paper foil covered with a water washable adhesive layer receives by printing a film which carries a well defined coloured pattern to be transferred to the skin. It is damped so as to reduce the adherence between the film and the paper and the protective layer is removed which normally covers said film, which is then applied to the eyelid. It is not make-up properly speaking.

With transfer methods it is not possible to cause the contour of the coloured zones to coincide accurately with that of the eyelid or of the skin portion to be made up. Furthermore, the adhesive adheres to the skin and must be removed without damaging the pattern, which is delicate and requires the paint used to have a special composition resisting washing: so it is not a question of traditional make-up pigments.

The invention overcomes these drawbacks of known methods by using a relatively flexible pre-cut support on which powdery coloured make-up pigments or lacquers are deposited so as to form a pigmented zone having the contours of the skin portion to be made up and the distribution of the colour densities required for obtaining the final make-up effect; the adherence of the pigments with each other and with the support being weaker than their adherence to the skin so that transfer thereof to the skin takes place by simply applying the support on the skin portion to be made up.

Other features and advantages of the invention will be clear from the following description.

Figure 1:
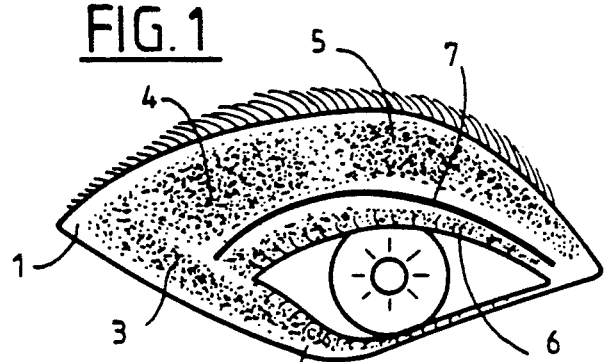
FIG. 1 shows a make-up device in accordance with the invention, applied about the contour of an open right eye.

In FIG. 1, the flexible support 1 is pre-cut so as to be applied exactly about the open right eye and is covered with pigments, in regions 2 to 6, of different colours chosen as a function of the colour of the eyes and the complexion of the face.

A concentration of pigments along a line 7 gives the impression of a colour line similar to that obtained traditionally using a special pencil.

Figure 2:
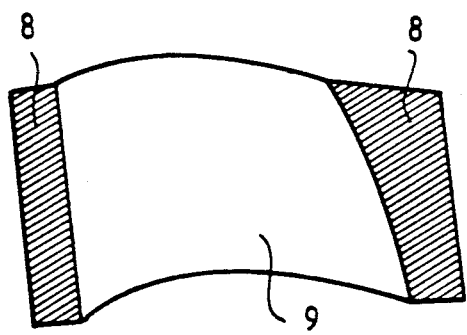
FIG. 2 shows schematically a make-up device intended for the left eyelid.
Figure 3:
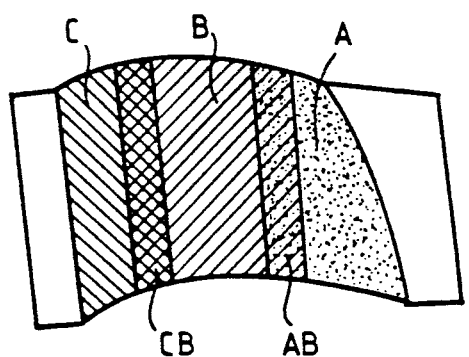
FIG. 3 illustrates one embodiment of a pigmented zone in which the pigments are distributed over the support in a plurality of deposition zones which partially overlap.

In FIG. 2, a flexible pre-cut support has been shown for application exactly on the eyelid of the closed left eye and comprises a non pigmented zone 8 and a pigmented zone 9. FIG. 3 shows that this latter is itself divided into zones of different colours A, B and C with partial overlapping AB and CB.

The support is advantageously not woven, for example formed of viscose fibres bonded chemically together by latex. Such a product is easy to cut out and has a flexibility, variable depending on the type but sufficient to exactly fit, at the time of application, to the shape of the region to be made up. It is preferably an absorbent product but one face of which is made non absorbent by a polyethylene film. It has a good breakage strength, does not crease and is not excessively deformable, which would cause an uneven distribution of the pigment on the skin, is pleasant to the feel and is resistant to the binder.

The pigments or lacquers are retained on the support stably in the presence of shaking or shocks, by an adhesive which is not toxic for the skin or the eye. It is an adhesive which can be redeposited, applied on the support then dried before receiving the pigments or lacquers. It permits correct release of the pigments which it adsorbs without preventing them from being redeposited.

The adhesive is absorbed by the support but does not pass therethrough because of the polyethylene film; as opposed to a conventional adhesive, it does not diffuse through the different pigment or lacquer strata.

The pigments or lacquers are solid coloured materials currently used in cosmetics.

In a way known per se, binders are incorporated with the monochrome colouring substances, such as mineral or vegetable oils, fatty esters and hydrophilic products of polyol type, these latter facilitating removal of the make-up with water.

Each monochrome dye is dispersed in an appropriate binder by means of a high-speed turbine and complex colours are obtained by simply mixing several of the monochrome powders thus obtained. The mixture is homogenized by means of a high-speed turbine, and at the same time a fixing agent, a plasticiser, preservers and perfumes are added thereto in a way known per se.

The fixing agent, advantageously hydrosoluble polyvinylpyrrolidone, used in a proportion less than 1% in the finished product so as to maintain the flexibility thereof and which has the further property of binding the pigments, has especially the function of protecting the surface of the make-up against manual contact. It is soluble in the applicator cream with which the skin will be advantageously covered before application of the device, so as to provide a better adherence of the pigments or lacquers.

The plasticiser agent, for maintaining the flexibility of the product during handling, and used at a concentration of about 0.1%, may be of different known types.

The applicator cream, which has a very good solvent power with respect to the binders associated with the pigments (pigment dispersing effect), thus making use of the product easy without the user having to apply pressures which are too high, contains for this paraffin oil or castor oil, to which vegetable oils are added which confer thereon a good cosmetic feel and 2 to 10% of non ionic emulsifiers (this proportion giving the minimum of toxicity for the eye).

Figure 7:
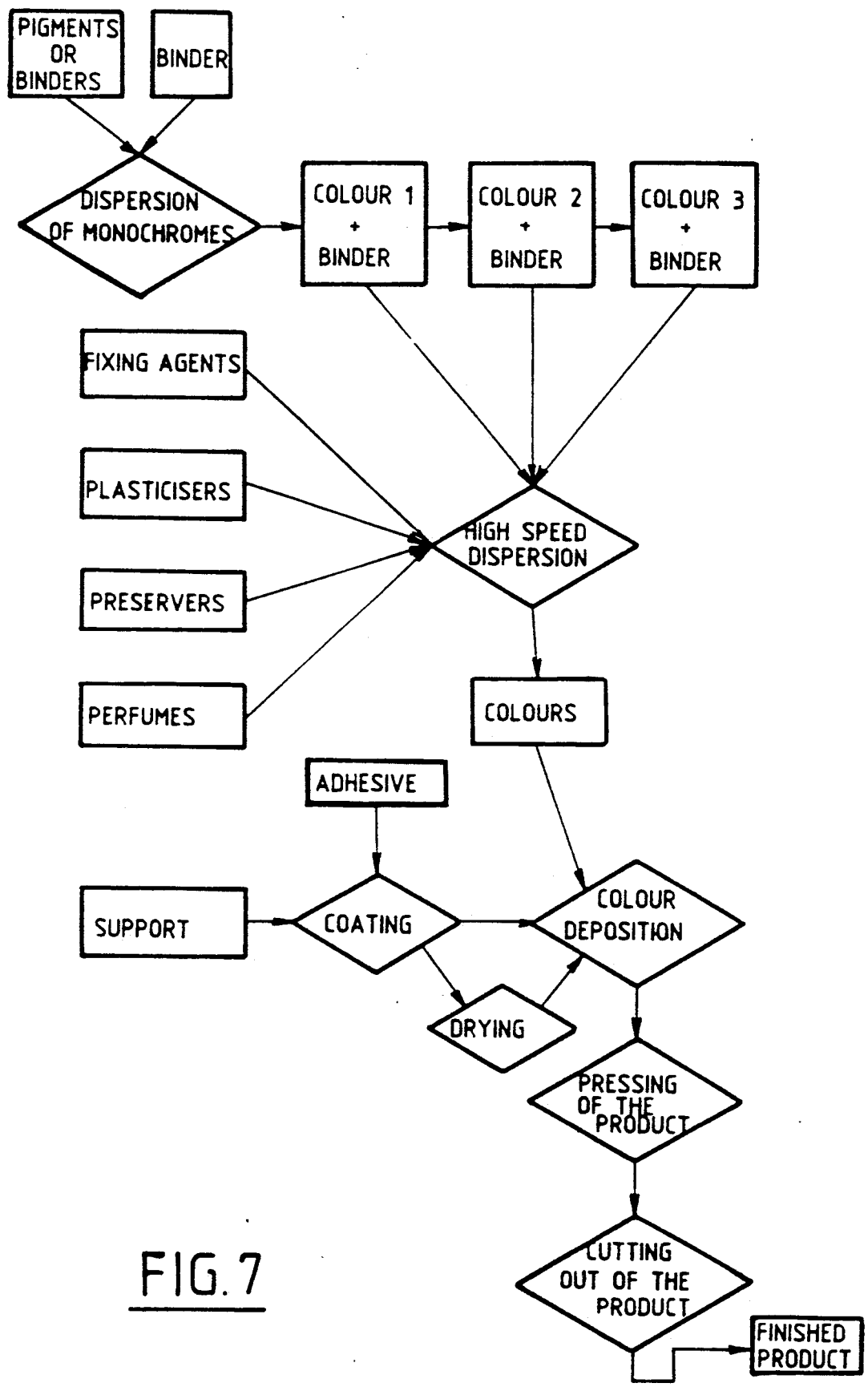
FIG. 7 is a flowchart of the operations for manufacturing the device.
Figure 8:
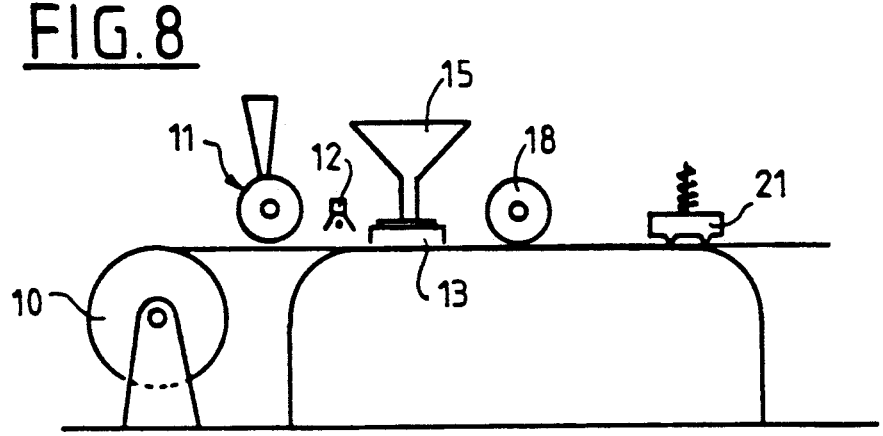
FIG. 8 shows one example of a manufacturing line.

The method of manufacture is illustrated in FIG. 7 and the manufacturing line in FIG. 8.

A support strip travels continuously from a roll 10.

Application of adhesive to the support is provided by a simple roller 11 of ink application type.

Drying may be carried out extemporaneously by passing the strip through a tunnel 12 at 40° C. or by means of a hot air stream.

Figure 4:
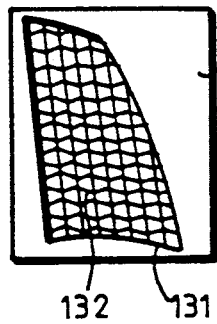
FIGS. 4 to 6 show the different matrices used successively for forming the deposition zones illustrated in FIG. 3.
Figure 5:
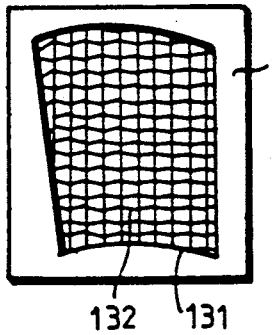
Figure 6:
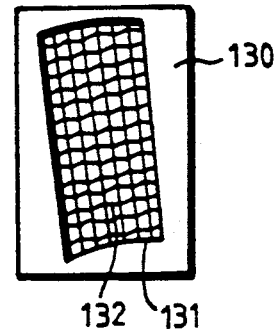

The form of each colour deposition zone (A, B, C) is defined by a specific matrix 13, such as those shown in FIGS. 4 to 6 which each comprise a body 130 having a cut-out 131 of corresponding shape and covered by a grid 132 through which the pigments or lacquers may pass to be distributed homogeneously.

Figure 9:
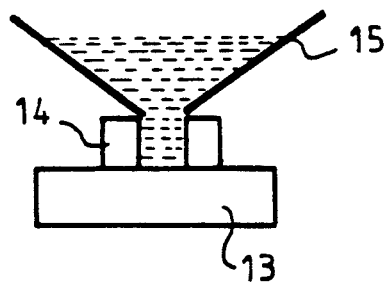
FIGS. 9 to 11 show embodiments of the pigment supply device.
Figure 11:
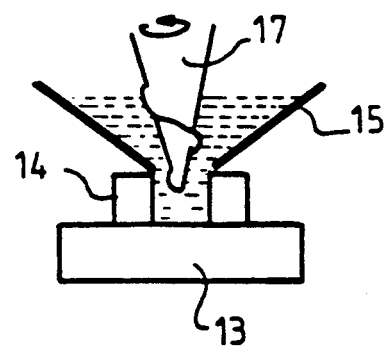
Figure 10:
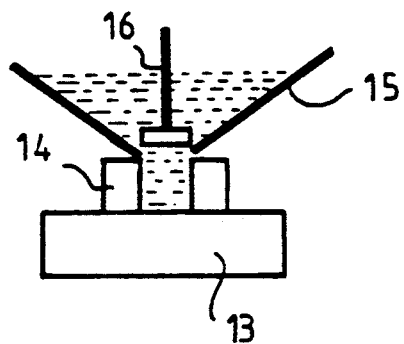

The supply device 14 for matrices 13 (FIG. 8), more particularly shown in FIGS. 4 to 6, makes it possible to deposit the pigments in fixed amounts. It comprises a supply shoe 14 (FIGS. 9 to 11) associated with a pigment reservoir 15.

A pusher piston 16 (FIG. 10) or an endless screw 17 (FIG. 11) may push the dye towards the grid.

As shown in FIG. 3, the matrices shown in FIGS. 4 to 6 may be used successively for obtaining the desired pigmented zone in which the colours are juxtaposed, with possible partial overlapping AB, CB of zones A, B, C; in order to obtain a colour graduation, it is then sufficient to pass a brush over the made up region.

Figure 12:
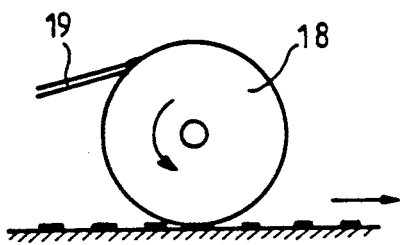
FIGS. 12 and 13 show two embodiments of the pressing device.

The dye layer is homogenized in thickness by means of a presser roller 18 (FIGS. 8 and 12) which compacts the pigment on the strip. A cleaning device 19 is associated with the roller.

Figure 13:
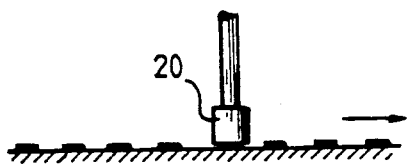

In a variant, a reciprocating piston 20 may be used (FIG. 13).

Figure 14:
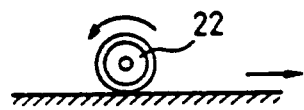
FIGS. 14 to 16 show embodiments of the cutting device.
Figure 15:
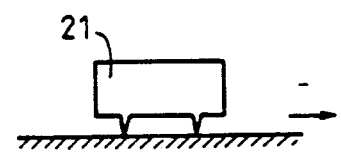
Figure 16:
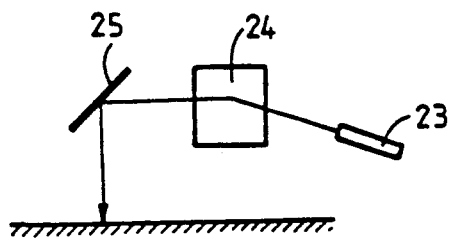

The product is cut out either using a punch having the shape 21 (FIGS. 8 and 15) or continuously by means of circular knives 22 (FIG. 14) or by means of a laser beam obtained from a generator 23 (FIG. 16) associated with mirrors 24, 25.

The compacted dye layer comprises several strata and the one which comes into contact with the skin is transferred thereto. The inner stratum the closest to the surface of the support is not transferred and remains bonded to the support: there is therefore no contact of the adhesive with the skin.

The zones not covered with pigment 8 (FIG. 2) facilitate the accurate positioning of the device on the region to be made up. Application is easy and immediate and removal of the support after deposition takes place readily without damaging the make-up. The aesthetic effect is entirely determined by the selection of the pigments and the arrangement of the colours made during manufacture.

A make-up assembly may comprise a set of pre-cut out supports for adapting to the different regions to be made up: cheeks, temples, eyes, eyelids and others, while taking into account the different morphologies of faces, and for each region to correspond to different coloured characteristic ranges as a function of the person, the desired make-up effects and fashion.

I claim:

1. A make-up device comprising a set of pre-cut out supports adapted to match the surface of different portions of a person's skin, in any of a plurality of arbitrary designs and patterns of colour, each of said supports having deposited thereon a pigmented layer of powdery coloured pigments or lacquers of the cosmetic type bonded together by means of binders, said layer having an outer surface stratum of coloured pigments or lacquers and an underlying stratum which is in contact with the support, said outer surface stratum having a cohesive power with respect to said underlying stratum, said underlying stratum having an adhesive power with respect to said support, said cohesive power being such that said outer surface stratum is transferred to the skin when it comes into contact with the skin, and said adhesive power being such that said underlying stratum remains bonded to the support preventing contact of adhesive with the skin.

2. A make-up device as claimed in claim 1, wherein said support is formed by a foil of an absorbent non-woven fabric coated on one side with a polyethylene film.

3. A make-up device as claimed in claim 1, wherein a further layer of a liquid adhesive adapted to be redeposited is inserted between the support and the pigmented layer.

4. A make-up device as claimed in claim 1, wherein said support further comprises non pigmented zones designed for facilitating the positioning of said support on a predetermined region of the person's skin.

5. A method of make-up by transferring coloured materials on to the skin from a relatively flexible support applied to the skin and removed after transfer, said method comprising the steps of:
    i. pre-cutting out said support;
    ii. depositing on said support powdery coloured pigments or lacquers of the cosmetic type bonded together by means of binders to form a pigmented layer having the contour of a predetermined region of the skin, with a distribution of the respective powdery coloured pigments or lacquers and of their respective densities in said zone so as to obtain the final make-up effect, said layer having an outer stratum in which the adherence of the pigments or lacquers with each other and with the support is weaker than their adherence to the skin and
    iii. transferring said pigmented layer to the skin by application of at least said outer stratum of the support provided with the pigmented layer on the skin portion to be made up and removal of the support.

6. A method according to claim 5, further comprising the prior step of applying on the skin a cream having a high solvent power with respect to said binders.

7. Method according to claim 5, wherein said support is formed by a foil of non woven fabric.

8. A method according to claim 7, wherein the non woven fabric is formed of viscose fibres bonded chemically by means of latexes.

9. A method according to claims 7 or 8, wherein the non woven fabric is absorbent and the foil is coated on one side with a polyethylene film.

10. A method according to claim 5, further comprising the step of coating the support with an adhesive before depositing the pigments or lacquers, said adhesive being a liquid adhesive adapted to be redeposited.

11. A method according to claim 5, wherein the said pigments or lacquers are prepared by dispersing in said binders respective monochrome coloured constituents of each pigment or lacquer and subsequently mixing said constituents.

12. A method according to claim 5, wherein the step of depositing the pigments or lacquers comprises the deposition, in predetermined amounts, of each coloured constituant of said pigments or lacquers in a predetermined deposition zone of the support and subsequently compacting the coloured constituants by pressing.

13. A method according to claim 12, wherein the respective deposition zones are partially overlapping on the support.

* * * * *